United States Patent

Hoeffkes et al.

Patent Number: 5,114,428
Date of Patent: May 19, 1992

[54] HAIR DYE PREPARATION

[75] Inventors: Horst Hoeffkes, Duesseldorf; Fritz Lange, Essen; Dieter Schrader, Duesseldorf, all of Fed. Rep. of Germany

[73] Assignee: Henkel Kommanditgesellschaft auf Aktien, Duesseldorf, Fed. Rep. of Germany

[21] Appl. No.: 635,173

[22] PCT Filed: Jul. 5, 1989

[86] PCT No.: PCT/EP89/00771
§ 371 Date: Jan. 14, 1991
§ 102(e) Date: Jan. 14, 1991

[87] PCT Pub. No.: WO90/00386
PCT Pub. Date: Jan. 25, 1990

[51] Int. Cl.⁵ .................................. A61K 2/13
[52] U.S. Cl. ............................. 8/405; 8/406; 8/408; 8/416; 8/421; 8/636; 252/174.19; 252/529; 252/548; 424/70; 524/243
[58] Field of Search ............. 8/405, 406, 408, 416, 8/421, 636; 252/174.19, 529, 548; 424/70; 524/243

[56] References Cited
U.S. PATENT DOCUMENTS 4,157,388  6/1979  Christiansen et al. .......... 424/70
4,233,164  11/1980  Davis .......................... 252/8.75
4,381,919  5/1983  Jacquet et al. ................ 8/406
4,486,338  12/1984  Ootani et al. ............. 252/174.19
4,555,246  11/1985  Grollier et al. ................ 8/406
4,698,065  10/1987  Hoeffkes et al. ............... 8/416

Primary Examiner—A. Lionel Clingman
Assistant Examiner—William S. Parks
Attorney, Agent, or Firm—Ernest G. Szoke; Wayne C. Jaeschke; Norvell E. Wisdom, Jr.

[57] ABSTRACT

Liquid preparations for oxidation hair dyes, which contain soaps, water-soluble cationic polymers and hair dye intermediates in an aqueous or aqueous-alcoholic carrier, can be stabilized by amines corresponding to formula (C)

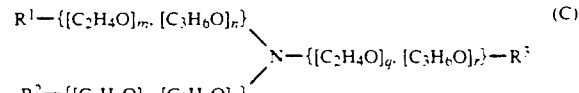

in which
$R^1$ is a $C_{8-22}$ alkyl group,
$R^2$ is hydrogen or a $C_{8-22}$ alkyl group,
$R^3$ is hydrogen except when $r=q=0$ and then is $C_{1-4}$ alkyl, and
m, n, o, p, q and r are numbers of 0 to 6.

20 Claims, No Drawings

HAIR DYE PREPARATION

BACKGROUND OF THE INVENTION

1. Field of the Invention

This invention relates to a liquid preparation for oxidation hair dyes. Preparations of the type in question consist of hair dye intermediates and a carrier suitable for application to the hair. Preferred carriers are cream-form emulsions of the water-in-oil type and aqueous or aqueous-alcoholic solutions of soaps.

2. Statement of Related Art

After addition to the aqueous solution of the oxidizing agent required to develop the oxidation dyes, oxidation hair dye bases of the type in question based on liquid, aqueous or aqueous-alcoholic soap solutions form a thickly liquid to gel-like, ready-to-use hair dye preparation.

It is also known that water-soluble cationic polymers can be added to hair dye preparations. The hair-cosmetic properties of the treated hair are improved in this way. At the same time, a hair-conditioning effect is obtained.

However, difficulties are involved in the production of liquid preparations for oxidation hair dyes containing soaps and cationic polymers because preparations such as these tend to become inhomogeneous and, in some cases, to become cloudy and to form precipitates and sediments immediately after their production or after prolonged storage. In addition, the hair-conditioning effect of the product is lost through interaction of the cationic polymer with the soap.

On the other hand, however, oxidation hair dye preparations based on liquid, aqueous or aqueous-alcoholic soap solutions represent an advantageous form of conditioning because, after addition to the aqueous solution of the oxidizing agent, they form a thickly liquid to gel-form dye preparation which adheres to the hair after application.

In order, therefore, to enable soaps and cationic polymers to be incorporated in hair dye bases, it was proposed in DE-OS 35 00 877 to use either dicarboxylic acids in the form of their water-soluble salts or amines corresponding to general formula (D)

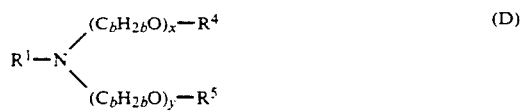

in which $R^1$ is a $C_{8-22}$ alkyl group and $R^4$ and $R^5$ independently of one another represent hydrogen or an acyl group having the formula $R^6$—COO—, where $R^6$ is a $C_{1<}$ alkyl or alkenyl group; b=2 or 3; and x and y are numbers of 0 to 5, the sum (x+y) being from 2 to 6, in order to stabilize the formulations.

Although the aqueous systems containing soap and cationic polymer can be stabilized by the substances mentioned with the conditioning properties of the cationic polymers intact, there remains the disadvantage that relatively high concentrations, particularly of the amine, have to be used to obtain the high viscosities required for stabilization.

Accordingly, the problem addressed by the present invention was to find stabilizing substances which, even when used in relatively low concentrations, would lead to a high increase in the viscosity of the formulation.

DESCRIPTION OF THE INVENTION

It has now surprisingly been found that certain amines having a structure differing from the amines of formula (D) exhibit the desired properties.

Accordingly, the present invention relates to a liquid preparation for oxidation hair dyes—consisting of hair dye intermediates and an aqueous or aqueous-alcoholic carrier—containing soaps (A) and water-soluble cationic polymers (B), characterized in that they contain amines corresponding to formula (C)

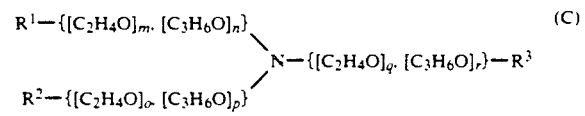

in which
$R^1$ is a $C_{8-22}$ alkyl group,
$R^2$ is hydrogen or a $C_{8>}$ alkyl group,
$R^3$ is hydrogen except when r=q=0 and then is $C_{1-4}$ alkyl, and
m, n, o, p, q and r are numbers of 0 to 6, for stabilization.

It has also surprisingly been found that a synergistic effect in regard to the increase in viscosity occurs when the amines mentioned are used in combination with amines corresponding to general formula (D)

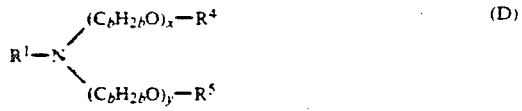

in which $R^4$ and $R^5$ independently of one another represent or an acyl group having the formula $R^6$—COO—, where $R^6$ is a $C_{1-21}$ alkyl or alkenyl group; b=2 or 3; and x and y are numbers of 0 to 5, the sum (x+y) being from 2 to 6.

Accordingly, liquid preparations for oxidation hair dyes containing a combination of amines (C) with amines (D) for stabilization are preferred.

Amines corresponding to formula (C) are already known as surfactants from DE-OS 35 04 242. However, there is no reference in this publication to any stabilizing effect on solutions containing soaps in addition to cationic polymers. According to the teaching of the cited publication, the amines corresponding to formula (C) may readily be obtained by reaction of, for example, hydroxyethyl dialkyl amines, hydroxypropyl dialkyl amines, dihydroxyalkyl alkyl amines or trihydroxyalkyl amines with sulfuric acid semiesters corresponding to the formula $R^7$—{$[OC_2H_4]_t$,$[OC_3H_6]_z$}—$OSO_3$—H, where $R^7$ is a $C_{8-22}$ alkyl group and t and z independently of one another are numbers of 0 to 6, with the proviso that t and z are not both 0, or alkali or alkaline earth metal salts thereof, in the presence of strong bases. Particulars of this production process can be found in the disclosure of the cited publication.

In addition, hydroxyl-terminated amines may be directly reacted with ethylene oxide and/or propylene oxide by known methods carried out at elevated temperature and elevated pressure using typical catalysts, such as sodium methylate. The amines obtained are also terminated by hydroxyl groups which, if desired, may be further reacted, for example with sulfuric acid semi-esters, by the process described above.

It is known to one skilled in the art that alkoxylation reactions, such as for example the addition of n moles ethylene oxide onto 1 mole of a compound containing an active hydrogen atom by known ethoxylation processes, do not give an individual adduct, but instead a mixture of residual quantities of free starting compound and a number of homologous (oligomeric) adducts of 1, 2, 3, . . .n, n+1, n+2 . . . etc. molecules of ethylene oxide per molecule of starting compound. The average degree of ethoxylation (n) is defined by the starting quantities of compound containing an active hydrogen atom and ethylene oxide. The distribution curve of the homolog mixture generally has a maximum in the range from n−3 to n+3. More detailed information on these points can be found, for example, in the journal *Soap/Cosmetics/Chemical Specialties*, January 1988, page 34.

Accordingly, where the products mentioned in this text have been produced by addition of ethylene oxide and/ or propylene oxide onto corresponding starting compounds and used without further fractionation of the product mixture, the degrees of alkoxylation mentioned are the average degrees of alkoxylation of the product mixture present.

Particularly good stabilizing effects are exhibited by amines in which $R^1$ is a $C_{16-18}$ alkyl group; $R^2$ is hydrogen or a $C_{16-18}$ group; and $R^3$ is hydrogen or, where $r=q=0$, is methyl; and m, o, r are numbers of 0 to 3 and n, p, q are numbers of 0 to 1.5. The better stabilizing effects are normally shown by amines of which the degrees of ethoxylation and/or propoxylation are in the lower range of the values indicated for the indices m to r.

So far as the terminal alkyl chains are concerned, the amines may be both individual products and also mixtures. Mixtures will generally be present when natural, renewable raw materials, such as oils and fats, are used as the source for these alkyl groups. Thus, amines containing a mixture of cetyl and stearyl groups, in a ratio of 1:4 to 2:1, as the alkyl groups, of the type obtainable for example from vegetable or animal tallow, show very good stabilizing properties. Accordingly, particularly preferred amines for the purposes of the present invention are, for example, (cetyl/stearyloxyethyl)-dihydroxyethyl amine (C1).

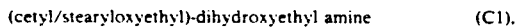

bis-(cetyl/stearyloxyethyl)-hydroxyethyl amine (C2)

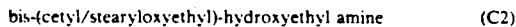

also compounds corresponding to the following formulae

In the above formulae, $C_{16/18}H_{33/37}$ stands for mixtures of alkyl groups consisting predominantly of cetyl ($C_{16}H_{33}$) and stearyl ($C_{18}H_{37}$) groups.

Amines corresponding to formula (D) above, in which $R^1$, $R^4$, $R^5$, b, x and y are as defined above, may be obtained from primary $C_{8-22}$ fatty amines by addition of (x+y) moles ethylene oxide or propylene oxide, for example in accordance with DE-PS 552 268.

Both pure fatty amines and also mixtures of fatty amines may be used for this purpose. Amine mixtures obtained by known methods from natural fats and oils are preferably used. Coconut oil alkyl amine is mentioned as an example. Fatty amines corresponding to general formula (D), in which $R^4$ and $R^5$ represent hydrogen, are initially obtained by addition of ethylene oxide or propylene oxide onto the fatty amines mentioned. These products may be converted into the products corresponding to general formula (D), in which $R^4$ and $R^5$ represent an acyl group having the formula $R^6$—COO—, by esterification with carboxylic acids having the general formula $R^6$-COOH, in which $R^6$ is a $C_{1-21}$ alkyl group, or with methyl esters or acid chlorides of these carboxylic acids. Numerous products corresponding to general formula (D) are commercially available. An adduct of 3 moles ethylene oxide with a $C_{12-14}$ fatty alcohol is marketed, for example, under the name LOWENOL®C-243. A bis-(2-hydroxyethyl)-soybean alkyl amine dioleate is available under the name LOWENOL®S-216. Other fatty amine alkoxylates are commercially available under the names ARAPHEN®GENAMIN®, MARLAZIN®and LUTENSOL®.

Preferred soaps (A) are water-soluble soaps of fatty acids. Fatty acids which are liquid at 20° C. are particularly suitable for this purpose. Fatty acids such as these are, for example, unsaturated linear fatty acids, such as oleic acid, linoleic acid, palmitoleic acid, erucic acid or liquid mixtures of these fatty acids with one another and with small amounts of saturated, linear $C_{12-22}$ fatty acids. Other particularly suitable liquid fatty acids are branched fatty acids, for example 2-hexyldecanoic acid, 2-octyldodecanoic acid, or isostearic acid.

Alkali hydroxides and alkali carbonates, ammonia and mono-, di- and tri-alkanolamines containing 2 to 4 carbon atoms in the alkanol group are suitable for converting the fatty acids into water-soluble soaps. Oleic acid in the form of the ammonium, mono-, di- and tri-ethanolammonium soap is particularly suitable.

In principle, the water-soluble cationic polymers (B) may be any polymers having a molecular weight in the range from 1,000 to 3,000,000 which either contain free or alkyl-substituted amino groups or quaternary ammo-

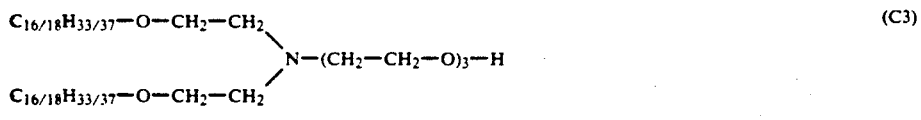

(C3)

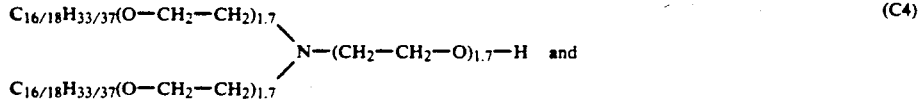

(C4)

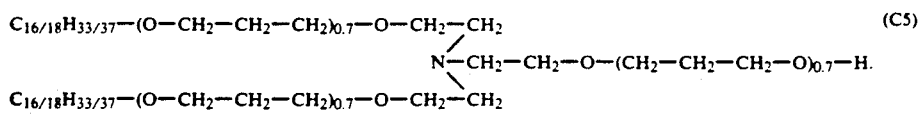

(C5)

nium groups in the polymer chain or bear primary, secondary or tertiary amino groups or quaternary ammonium groups attached to the polymer chain either directly or by intermediate members. These amino groups or quaternary ammonium groups may also be members of 5- or 6- membered ring systems, for example the morpholine, pyridine, piperazine, or imidazole ring system. Numerous examples of such water-soluble cationic polymers can be found, for example, in DE-OS 28 11 010. In addition, many other water-soluble cationic polymers are known from the literature.

Water-soluble homopolymers or copolymers (Bl) containing units corresponding to the following general formula

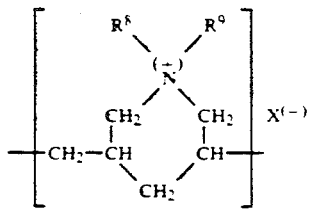

in which $R^8$ and $R^9$ are $C_{1-4}$ alkyl groups or $C_{2-4}$ hydroxyalkyl groups and $X^{(-)}$ is a chloride, bromide, hydrogen sulfate, methoxysulfate, phosphate, or acetate ion, are particularly suitable. Examples of cationic polymers of this type are, for example, the commercial products MERQUAT®100 and MERQUAT®550 (Quaternium 41). The production of these polymers is known, for example, from DE-OS 21 09 081.

Other particularly suitable cationic polymers are cellulose ethers (B2), of which the anhydroglucose units contain 1 to 3 substituents containing quaternary ammonium groups which are attached by ether oxygen. Polymers such as these are known, for example, from DE-OS 15 93 657. A commercial product of this type is, for example, POLYMER JR®400.

The quaternary polymeric urea derivatives (B3) known from U.S. Pat. No. 4,157,388 are also particularly suitable. A commercially available product of this type is MIRAPOL®A15 which consists of structural units corresponding to the following general formula diate components with one another or with one or more coupler components in the presence of an oxidizing agent. The primary intermediates used are normally primary aromatic amines containing another free or substituted hydroxy or amino group in the para- or ortho-position, diaminopyridine derivatives, heterocyclic hydrazone derivatives, 4-aminopyrazolone derivatives, or tetraaminopyrimidines. The so-called couplers used are, for example, m-phenylenediamine derivatives, phenols, naphthols, resorcinol derivatives, or pyrazolones. The hair dye preparations according to the invention may contain the oxidation hair dye intermediates in a quantity of 0.05 to 5.0% by weight and preferably in a quantity of 0.2 to 2.0% by weight.

The hair dye preparations according to the invention may contain synthetic anionic, nonionic, ampholytic or zwitterionic surfactants in quantities of up to 20% by weight as further auxiliaries. Suitable auxiliaries of this type are, for example, linear alkyl sulfates containing 12 to 18 carbon atoms in the alkyl group, alkyl polyglycol ether sulfates containing 12 to 16 carbon atoms in the alkyl group and 1 to 6 glycol ether groups in the molecule, fatty alcohol polyglycol ethers obtained by addition of 6 to 20 moles ethylene oxide onto $C_{10-18}$ fatty alcohols, adducts of 6 to 20 moles ethylene oxide with nonyl or dodecyl phenol, fatty alkyl dimethyl amine oxides, fatty acid mono- or di-ethanolamines, N-fatty alkyl diethyl glycine, N-fatty alkyl aminopropionic acid and other known surfactants.

In addition, the hair dye preparations according to the invention may contain 0 to 20% by weight $C_{12-22}$ fatty alcohols, for example coconut oil fatty alcohol, lauryl alcohol, myristyl alcohol, cetyl alcohol, oleyl alcohol or stearyl alcohol in emulsified form. Synthetic branched alcohols, for example 2-octyl dodecanol, 2-hexyl decanol, isostearyl alcohol, isohexadecyl alcohol, are also suitable.

The hair dye preparations according to the invention preferably contain lower $C_{1-4}$ alcohols and/or lower $C_{2-6}$ glycols, for example ethanol, isopropanol, n-propanol, ethylene glycol, 1,2-propylene glycol, methyl glycol, ethyl glycol, butyl glycol, diethylene glycol, dipropylene glycol, or hexylene glycol. These lower alcohols or glycols are preferably present in the preparations in a total quantity of 1 to 30% by weight. The

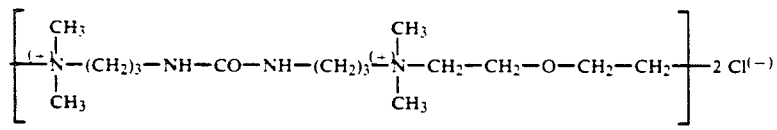

the average degree of polymerization being approximately 6.

According to the invention, preferred liquid preparations are those which contain 1 to 30% by weight soaps (A), 0.5 to 10% by weight water-soluble cationic polymers (B), 0.1 to 20% by weight and more particularly 0.5 to 10% by weight amines (C) and 0 to 20% by weight and more particularly 0 to 5% by weight amines (D).

In addition to the carrier components mentioned, the hair dye preparations according to the invention contain oxidation hair dye intermediates. The known dye bases or primary intermediate compounds and known modifiers or coupler compounds are used as the oxidation dye intermediates. The oxidation dyes are formed by oxidative coupling of one or more primary intermeaddition of these lower alcohols and/or polyols keeps the preparations thinly liquid and readily processable at 20° C.

A thickly liquid to gel-form, ready-to-use hair dye preparation is only formed after the addition of a substantially equivalent quantity of water or aqueous hydrogen peroxide solution, which is carried out shortly before application to the hair to develop the dye.

In addition to the components mentioned above, the hair dye preparations according to the invention also contain the additives typically present in oxidation dye bases of the type in question for stabilizing the oxidation dye intermediates. Such additives are complexing agents, for example ethylenediamine tetraacetic acid, nitrilotriacetic acid, 1-hydroxyethane-1,1-diphosphonic acid, or other organodiphosphonic acids in the form of their alkali salts; antioxidants, such as for example sodium sulfite, sodium bisulfite, hydroquinone or salts of thioglycolic acid or ascorbic acid; buffer salts, for example ammonium sulfate, ammonium carbonate, ammonium citrate, and ammonia or an alkanolamine for establishing a pH value in the range from 8 to 10.

The following Examples are intended to illustrate the invention with limiting it in any way.

EXAMPLES

I Preparation of the amines (C)

a) Amine C1

21 kg SULFOPON®T55 (tallow fatty acid alcohol sulfate sodium salt, essentially $C_{16}$ and $C_{18}$ alkyl chains in a ratio of 30:70, active substance content about 55%) were added in portions in a water jet vacuum at temperatures of around 80° to 100° C. to 10.7 kg (72 moles) triethanolamine and dehydrated in the process. After purging with nitrogen gas, 1.46 kg (36.5 moles) NaOH were added. The mixture was then heated for 5 hours at 170° C. and subsequently cooled to 90° C.

After the product had been washed with hot water and impurities and secondary products removed by application of vacuum at about 110° C., amine C1 was obtained in a yield of 12.5 kg (99.7% of the theoretical). The amine value of the product was 135.1 (calculated 136.0).

b) Amine C2

13.4 kg SULFOPON®T55 (tallow fatty alcohol sulfate salt, essentially $C_{16}$ and $C_{18}$ alkyl chains in a ratio of 30:70, active substance content about 55%) were added at about 85° C. to 8.0 kg amine C1. The water present in the mixture was then distilled off in vacuo at around 100° C. After addition of 0.8 kg NaOH, the reaction time was 3 hours at 170° C. in a nitrogen atmosphere. After the product had been washed with hot water and impurities and secondary products removed by application of a vacuum at around 110° C., amine C2 was obtained in a yield of 94.2% of the theoretical. The amine value of the product was 84 (calc. 83.4).

c) Amine C3 c1) 10.4 kg (70 moles) triethanolamine, 20 kg (58.3 moles) LANETTE®E (sodium cetyl stearyl (1:1) sulfate, min. 90% active substance) and 2.8 kg NaOH were reacted in the same way as in a). 16.2 kg of the product were reacted with 14.9 kg LANETTE®E and 2.09 kg NaOH in the same way as in b). The amine value of the product obtained was 84 (calc. 94).

c2) To 676 g (1 mole) of the product thus obtained, in an autoclave, were added 5.1 g sodium methylate solution (0.2% by weight sodium methylate, based on the total quantity of starting materials, amine and ethylene oxide). The autoclave was then purged with nitrogen and evacuated for 30 minutes at 100° C. 88 g (2 moles) ethylene oxide were then introduced under a pressure of 5 bar and at a temperature of 150° C. Following an after-reaction lasting 30 minutes, the residual ethylene oxide was removed at 75° C. by application of a vacuum. The yield of amine C3 was 755 g 99% of the theoretical). The amine value of the product was 73 (calc. 82).

d) Amine C4

In an autoclave, 746 g triethanolamine were reacted with 440 g ethylene oxide in the presence of 2.9 g sodium methylate solution as catalyst at a temperature of 150° C. and under a pressure of 5 bar in the same way as in c2). A total of 1446 g (4.22 moles) LANETTE®E and 169 g (4.22 moles) NaOH were added in portions in equivalent quantities to 500 g (2.11 moles) of the product at 150 to 175° C. The product formed thereafter served as solvent, so that the reaction mixture remained stirrable. After the last portion of LANETTE®E and NaOH had been added, the after-reaction time was 3 hours at 175° C. The reaction mixture was then worked up as in a). Amine C4 was obtained as the end product in a yield of 85% of the theoretical. The amine value of the product was 83.1 (calc. 82.1).

e) Amine C5

Triethanolamine was reacted with twice the molar quantity of propylene oxide as in c2). 530.4 g (2 moles) of the product thus obtained were reacted with four portions of 343 g (1 mole) LANETTE®E and 40 g (1 mole) NaOH. After the water had been removed in vacuo, the reaction time was 3 hours at 150° C. The reaction mixture was worked up as in a). 1205 g (85% of the theoretical) of amine C5 were obtained as the end product. The amine value of the product was 76.5 (calc. 78.8).

II. Performance Test

Preparations having the following composition were tested:

| Component | Parts by weight |
| --- | --- |
| Oleic acid | 1.5 |
| TEXAPON ®N 25[1] | 4.0 |
| DEHYTON ®K[2] | 3.0 |
| POLYMER JR ®400[3] | 1.0 |
| Amine (C)[4] | see Table 1 |
| Amine (D)[5] | see Table 1 |
| Propylene glycol | 2.15 |
| Dye intermediates | |
| resorcinol | 0.24 |
| 4-chlororesorcinol | 0.11 |
| p-aminophenol hydrochloride | 0.06 |
| 2,4-dichloro-3-aminophenol hydrochloride | 0.035 |
| p-phenylenediamine | 0.26 |
| Stabilizing components | |
| ammonium sulfate | 0.75 |
| TURPINAL ®SL[6] | 0.2 |
| sodium sulfite | 0.5 |
| sodium ascorbate | 0.5 |
| Conc. ammonia | to pH 10 |
| Water | ad 100 |

[1]TEXAPON ®N 25: $C_{12-14}$ fatty alcohol +2 ethylene oxide sulfate, sodium salt (28% by weight water) (Henkel)
[2]DEHYTON ®K- fatty acid amide derivative of coconut oil having a betaine structure and corresponding to the formula R—CONH—(CH$_2$)$_3$—N$^+$(CH$_3$.)$_2$—CH$_2$—COO$^-$ (about 30 by weight in water) (Henkel)
[3]POLYMER JR ®400: cationic cellulose derivative (Union Carbide)
[4]Amine (C): compound C2
[5]Amine (D): coconut oil alkyl amine +2 ethylene oxide obtainable by addition of 2 moles ethylene oxide with coconut oil alkyl amine, for example in accordance with DE-OS 552 268
[6]TURPINAL ®SL: hydroxyethane-1,1-diphosphonicacid (Henkel)

To produce the oxidation hair dye preparation, TEXAPON®DEHYTON®K, oleic acid, propylene glycol and, optionally, amine (C) and/or amine (D) were first mixed and then heated in a water bath to approximately 80 C. (mixture A). The dye intermediates were mixed and dissolved in 10 parts by weight distilled water at 90° C. with addition of 0.5 to 2 parts by weight concentrated ammonia solution (mixture B). The stabilizer salts were also mixed and 0.2 part by weight concentrated ammonia solution was added. The TUR-PINAL®SL was then added together with distilled water at 90° C., after which more distilled water was added to the solution until it contained a total of 10 parts by weight water. A clear solution of the salts and the complexing agent was formed (mixture C).

First mixture C and then mixture B were then introduced with stirring into mixture A. 20 parts by weight of a 5% by weight solution of POLYMER JR ®400 (corresponding to 1 part by weight active substance) were then added with stirring, the viscosity of the mixture increasing significantly. Finally, the mixture was made up to a total of 100 parts by weight with distilled water.

These hair dye preparations are low-viscosity to medium-viscosity liquids of which the viscosities were determined with a Haake-Rotovisko RV 12 viscosimeter at 20° C.

The results are shown in Table 1.

TABLE 1

|  | Formulation 1 | Formulation 2 | Formulation 3 |
|---|---|---|---|
| Parts by weight amine (C) | — | 5.4 | 5.4 |
| Parts by weight amine (D) | 2.0 | — | 2.0 |
| Viscosity (mPas) | 700 | 2000 | 11100 |

Corresponding formulations which contained neither amine (C) nor amine (D) were not stable.

The results clearly reflect the stabilizing effect obtained by using amines (C) according to the invention as a result of the buildup of viscosity.

In addition, the synergistic effect obtained where these amines are combined with amines of formula (D) is clearly apparent.

After mixing 1 part by weight of formulations 1 to 3 with 1 part by weight of 6% by weight hydrogen peroxide solution, only formulations 2 and 3 showed entirely satisfactory adhesion to hair.

What is claimed is:

1. A liquid preparation of oxidation hair dyes comprising hair dye intermediates and an aqueous or aqueous-alcoholic carrier containing soaps (A) and water-soluble cationic polymers (B), wherein the improvement comprises the stabilization of the preparation by the presence therein of amines corresponding to formula (C):

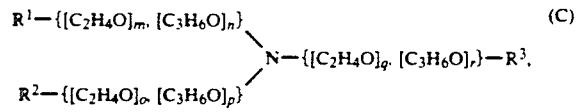

in which
m, n, o, p, q and r are numbers of 0 to 6,
$R^1$ is a $C_{8\text{-}22}$ alkyl group,
$R^2$ is hydrogen or a $C_{8>}$ alkyl group,
$R^3$ is hydrogen except when r=q=0 and then is $C_{1\text{-}4}$ alkyl, and
if m=n=0, $R^2$ and $R^3$ are not both hydrogen.

2. A liquid preparation as claimed in claim 1, additionally stabilized by the present of amines corresponding to formula (D):

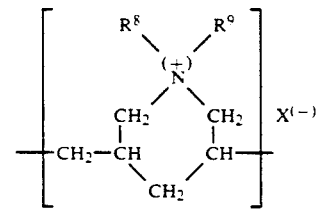

in which $R^1$ has the same meaning as in claim 1 and $R^4$ and $R^5$ independently of one another represent hydrogen or an acyl group having the formula $R^6$—COO—, where $R^6$ is a $C_{1\text{-}21}$ alkyl or alkenyl group; b=2 or 3; and x and y are numbers of 0 to 5, the sum (x+Y) being from 2 to 6.

3. A liquid preparation as claimed in claim 2, comprising water-soluble soaps of $C_{12\text{-}22}$ fatty acids as the soaps (A) and a polymeric quaternary ammonium compound selected from the group consisting of:

(B1) water-soluble homopolymers and copolymers containing units corresponding to the following general formula

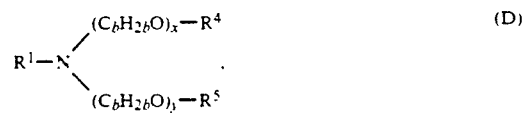

in which $R^8$ and $R^9$ are $C_{1\text{-}4}$ alkyl groups or $C_{2\text{-}4}$ hydroxyalkyl groups and $X^{(-)}$ is a chloride, bromide, hydrogen sulfate, methoxysulfate, phosphate, or acetate ion;

(B2) cellulose ethers of which the anhydroglucose units bear 1-3 substituents containing quaternary ammonium groups which are attached by ether oxygen, (B3) polymeric quaternary urea derivatives containing units corresponding to the following general formula:

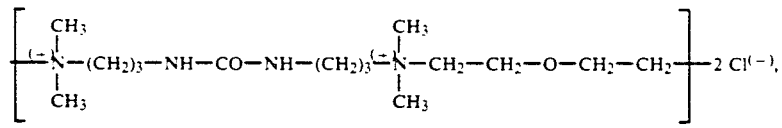

as the water-soluble cationic polymer (B).

4. A liquid preparation as claimed in claim 3, comprising:
1 to 30% by weight soaps (A),
0.05 to 10% by weight water-soluble cationic polymers (B),
0.1 to 20% by weight amines (C), and
not more than 20% by weight amines (D).

5. A liquid preparation as claimed in claim 4, comprising:
1 to 30% by weight soaps (A),
0.05 to 10% by weight water-soluble cationic polymers (B),
0.05 to 10% by weight amines (C), and
not more than 5% by weight amines (D).

6. A liquid preparation as claimed in claim 5, comprising amines corresponding to formula (C) in which $R^1$ is a $C_{16-18}$ alkyl group; $R^2$ is hydrogen or a $C_{16-18}$ alkyl group; $R^3$ is hydrogen or, if $r=q=0$, a methyl radical; m, o, and r are numbers of 0 to 3; n, p, and q are numbers of 0 to 1.5; and if $m=n=0$, $R^2$ and $R^3$ are not both hydrogen.

7. A liquid preparation as claimed in claim 6, comprising molecules selected from the group consisting of $C_{1-4}$ alcohols and $C_{2-6}$ glycols in a total quantity of 1 to 30% by weight.

8. A liquid preparation as claimed in claim 7, additionally comprising molecules selected from the group consisting of anionic, zwitterionic, and nonionic surfactants in a total quantity of 1 to 20% by weight.

9. A liquid preparation as claimed in claim 8, wherein the soaps (A) are selected from the group consisting of ammonium oleate and mono-, di-, and tri-ethanolammonium oleate.

10. A liquid preparation as claimed in claim 1, comprising water-soluble soaps of $C_{12-22}$ fatty acids as the soaps (A) and a polymeric quaternary ammonium compound selected from the group consisting of:

(B1) water-soluble homopolymers and copolymers containing units corresponding to the following general formula:

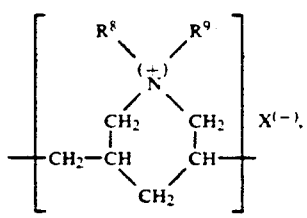

in which $R^8$ and $R^9$ are $C_{1-4}$ alkyl groups or $C_{2-4}$ hydroxyalkyl groups and $X^{(-)}$ is a chloride, bromide, hydrogen sulfate, methoxysulfate, phosphate, or acetate ion;

(B2) cellulose ethers of which the anhydroglucose units bear 1-3 substituents containing quaternary ammonium groups which are attached by ether oxygen, (B3) polymeric quaternary urea derivatives containing units corresponding to the following general formula:

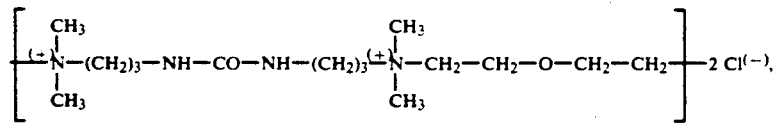

as the water-soluble cationic polymer (B).

11. A liquid preparation as claimed in claim 2, comprising:
 1 to 30% by weight soaps (A),
 0.05 to 10% by weight water-soluble cationic polymers (B),
 0.05 to 10% by weight amines (C), and
 not more than 5% by weight amines (D).

12. A liquid preparation as claimed in claim 1, comprising:
 1 to 30% by weight soaps (A),
 0.05 to 10% by weight water-soluble cationic polymers (B),
 0.05 to 10% by weight amines (C), and
 not more than 5% by weight amines (D).

13. A liquid preparation as claimed in claim 12, comprising amines corresponding to formula (C) in which $R^1$ is a $C_{16-18}$ alkyl group; $R^2$ is hydrogen or a $C_{16-18}$ alkyl group; $R^3$ is hydrogen or, if $r=q=0$, a methyl radical; m, o, and r are numbers of 0 to 3; n, p, and q are numbers of 0 to 1.5; and if $m=n=0$, $R^2$ and $R^3$ are not both hydrogen.

14. A liquid preparation as claimed in claim 11, comprising amines corresponding to formula (C) in which $R^1$ is a $C_{16-18}$ alkyl group; $R^2$ is hydrogen or a $C_{16-18}$ alkyl group; $R^3$ is hydrogen or, if $r=q=0$, a methyl radical; m, o, and r are numbers of 0 to 3; n, p, and q are numbers of 0 to 1.5; and if $m=n=0$, $R^2$ and $R^3$ are not both hydrogen.

15. A liquid preparation as claimed in claim 2, comprising amines corresponding to formula (C) in which $R^1$ is a $C_{16-18}$ alkyl group; $R^2$ is hydrogen or a $C_{16-18}$ alkyl group; $R^3$ is hydrogen or, if $r=q=0$, a methyl radical; m, o, and r are numbers of 0 to 3; n, p, and q are numbers of 0 to 1.5; and if $m=n=0$, $R^2$ and $R^3$ are not both hydrogen.

16. A liquid preparation as claimed in claim 1, comprising amines corresponding to formula (C) in which $R^1$ is a $C_{16-18}$ alkyl group; $R^2$ is hydrogen or a $C_{16-18}$ alkyl group; $R^3$ is hydrogen or, if $r=q=0$, a methyl radical; m, o, and r are numbers of 0 to 3; n, p, and q are numbers of 0 to 1.5; and if $m=n=0$, $R^2$ and $R^3$ are not both hydrogen.

17. A liquid preparation as claimed in claim 1, comprising molecules selected from the group consisting of $C_{1-4}$ alcohols and $C_{2-6}$ glycols in a total quantity of 1 to 30% by weight.

18. A liquid preparation as claimed in claim 1, additionally comprising molecules selected from the group consisting of anionic, zwitterionic, and nonionic surfactants in a total quantity of 1 to 20% by weight.

19. A liquid preparation as claimed in claim 2, comprising:
 1 to 30% by weight soaps (A),
 0.05 to 10% by weight water-soluble cationic polymers (B),
 0.1 to 20% by weight amines (C), and
 not more than 20% by weight amines (D).

20. A liquid preparation as claimed in claim 1, comprising:
 1 to 30% by weight soaps (A),
 0.05 to 10% by weight water-soluble cationic polymers (B),
 0.01 to 20% by weight amines (C), and
 not more than 20% by weight amines (D).

* * * * *

UNITED STATES PATENT AND TRADEMARK OFFICE
CERTIFICATE OF CORRECTION

PATENT NO. : 5,114,428
DATED : May 19, 1992
INVENTOR(S) : Hoeffkes et al.

It is certified that error appears in the above-identified patent and that said Letters Patent is hereby corrected as shown below:

In claim 1, column 9, line 65, "$C_8$>" should read -- $C_{8-22}$ --.

In claim 12, column 12, line 6, after "and" add -- optionally --.

In calim 12, column 12, line 7, "not more than" should read -- up to --.

In claim 20, Column 12, line 64, after "and" add -- optionally --.

In claim 20, column 12, line 65, "not more than" should read -- up to --.

Signed and Sealed this

Fifth Day of October, 1993

Attest:

BRUCE LEHMAN

*Attesting Officer*  *Commissioner of Patents and Trademarks*